(12) United States Patent
Grundler

(10) Patent No.: US 6,818,642 B2
(45) Date of Patent: Nov. 16, 2004

(54) BENZYLAMINOPYRIMIDINES

(75) Inventor: Gerhard Grundler, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/477,622

(22) PCT Filed: May 14, 2002

(86) PCT No.: PCT/EP02/05266

§ 371 (c)(1),
(2), (4) Date: Mar. 23, 2004

(87) PCT Pub. No.: WO02/094832

PCT Pub. Date: Nov. 28, 2002

(65) Prior Publication Data

US 2004/0152714 A1 Aug. 5, 2004

(30) Foreign Application Priority Data

Aug. 14, 2001 (DE) .......................... 101 39 825
Dec. 19, 2001 (DE) .......................... 101 62 319

(51) Int. Cl.$^7$ ................... C07D 487/04; C07D 403/12; A61K 31/505
(52) U.S. Cl. ...................... 514/248; 514/256; 544/236; 544/328
(58) Field of Search ................. 544/236, 328; 514/248, 256

(56) References Cited

FOREIGN PATENT DOCUMENTS

| EP | 0632040 A1 | 1/1995 |
|---|---|---|
| WO | WO 96/016656 | 6/1996 |
| WO | WO 98/028299 | 7/1998 |
| WO | WO 99/061439 | 12/1999 |
| WO | WO 01/034573 | 5/2001 |
| WO | WO 01/034578 | 5/2001 |

OTHER PUBLICATIONS

Douglas, Jr. Introduction to viral diseases, Cecil Texbook of Medicine, 20$^{th}$ Edition, vol. 2, pp. 1739–1747,1996.*

* cited by examiner

Primary Examiner—Deepak Rao
(74) Attorney, Agent, or Firm—Gary M. Nath; Todd L. Juneau; Sheldon M. McGee

(57) ABSTRACT

Benzylaminopyrimidine compounds of a certain general formula I, in which the substituents and symbols are as defined in the description, are suitable for controlling Helicobacter bacteria.

27 Claims, No Drawings

BENZYLAMINOPYRIMIDINES

FIELD OF THE INVENTION

The invention relates to compounds intended for use in the pharmaceutical industry as active principles for preparing medicaments.

STATE OF THE ART

International patent application WO 96/16656 describes compounds of a general formula A-X—R in which A may be a fused imidazolyl radical and R may be a nonaromatic hydrocarbon radical. European patent application EP 632040 describes further fused imidazoles which carry as substituent B a 5- or 6-membered fused or nonfused unsubstituted heterocycle. International patent application WO 98/28299 describes imidazopyridazines attached via a specific bridge in position 4 to a pyridine ring substituted in position 2. International patent application WO 99/61439 describes pyridylmethyl-aminopyrimidines substituted. In a special way in position 4. International patent applications WO 01/34573 and WO 01/34578 disclose compounds comprising primarily, on the one hand, S-substituted thiophenols with a benzimidazol-2-yl-thiomethyl radical in position 3 and, on the other hand, S- or O-substituted thiophenols and pyridinethiols or phenols and pyridinols, respectively, with an N-heterocyclylmethyl radical in position 3. All of the compounds specified in the above documents are said to be suitable for controlling Helicobacter bacteria.

DESCRIPTION OF THE INVENTION

The invention provides compounds of the formula I,

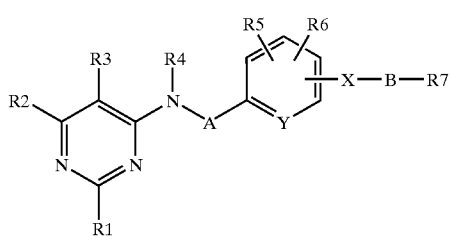

(I)

In which

R1 is hydrogen, 1–4C-alkyl or halogen,

R2 is hydrogen. 1–4C-alkyl or halogen,

R3 is hydrogen, 1–4C-alkyl or halogen,

R4 is hydrogen or 1–4C-alkyl,

R5 is hydrogen, hydroxyl, 1–4C-alkyl, 1–4C-alkoxy, wholly or predominantly fluorine-substituted 1–4C-alkoxy, trifluoromethyl or halogen.

R6 is hydrogen, hydroxyl, 1–4C-alkyl, 1–4C-alkoxy, wholly or predominantly fluorine-substituted 1–4C-alkoxy or halogen, R7 is a cyclic or bicyclic radical which is substituted by nitro and R9 and R10 and is selected from the group consisting of imidazole, imidazopyridazine and imidazopyridine, A is 1–7C-alkylene, B is a bond or 1–7C-alkylene, X is O (oxygen), N-1–4C-alkyl, NH or S(O)$_n$ and Y is CH or CR8, where R8 is hydroxyl, 1–4C-alkyl, 1–4C-alkoxy, wholly or predominantly fluorine-substituted 1-C-alkoxy, trifluoromethyl or halogen, R9 is hydrogen, 1–4C-alkyl, halogen, nitro, hydroxy-1–4C-alkyl or 1–4C-alkylcarbonyloxy-1–4C-alkyl, R10 is hydrogen, 1–4C-alkyl or nitro, and n is 0, 1 or 2, and salts thereof.

1–4C-Alkyl stands for straight-chain, branched or cyclic alkyl radicals having from 1 to 4 carbon atoms. Examples that may be mentioned include the butyl, isobutyl, sec-butyl, tert-butyl, cyclobutyl, propyl, isopropyl, cylopropyl, cyclopropylmethyl, ethyl, and methyl radicals.

Halogen for the purposes of the present invention is bromine, chlorine, and fluorine.

1–4C-Alkoxy stands for a radical which in addition to the oxygen atom contains one of the abovementioned 1–4C-alkyl radicals. Examples that may be mentioned include the cyclopropylmethoxy, methoxy, and ethoxy radicals.

Wholly or predominantly fluorine-substituted 1–4C-alkoxy stands for a 1–4C-alkoxy radical in which all or more than half of the hydrogen atoms have been replaced by fluorine atoms. Examples that may be mentioned include the 223,3,3-pentafluoropropoxy, the perfluoroethoxy, the 1,2,2-trifluoroethoxy, particularly the 1.1,2,2-tetrafluoroethoxy, the 2,2,2-trifluoroethoxy, the trifluoromethoxy, end, in particular, the difluoromethoxy radicals.

1–7C-Alkylene stands for straight-chain or branched 1–7C-alkylene radicals, examples being the methylene (—CH$_2$—), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—], 1-methylethylene [—CH(CH$_3$)—CH$_2$—], pentamethylene (—CH$_2$—CH$_2$—CH$_2$—CH$_2$—CH$_2$—), hexamethylene (—CH$_2$—CH$_2$—CH$_2$—CH$_2$—CH$_2$—CH$_2$—), and the heptamethylene (—CH$_2$—CH$_2$—CH$_2$—CH$_2$—CH$_2$—CH$_2$—CH$_2$—) radicals.

Hydroxy-1–4C-alkyl stands for the abovementioned 1–4C-alkyl radicals substituted by a hydroxyl group. Examples that may be mentioned include the 2-hydroxyethyl and 3-hydroxypropyl radicals and, in particular, the hydroxymethyl radical.

1–4C-Alkylcarbonyloxy radicals contain in addition to the oxygen atom one of the abovementioned 1–4C-alkylcarbonyl radicals. An example that may be mentioned is the acetoxy radical (CH$_3$CO—O—).

1–4C-Alkylcarbonyloxy-1–4C-alkyl stands for one of the abovementioned 1–4C-alkyl radicals substituted by one of the abovementioned 1–4C-alkylcarbonyloxy radicals. An example that may be mentioned is the acetoxymethyl (CH$_3$CO—O—CH$_2$—) radical.

As exemplary radicals R7 mention may be made of the 2-methyl-5-nitroimidazol-1-yl radical, the 2-methyl-nitroimidazol-1-yl radical, the 5-bromo-2-methyl-4-nitroimidazol-1-yl radical, the 4-nitroimidazol-1-yl radical, the 2-methyl-4,5-dinitroimidazol-1-yl radical, the 2,4-dinitroimidazol-1-yl radical, the 2-hydroxymethyl-5-nitroimidazol-1-yl radical, the 2-acetoxymethyl-5-nitroimidazol-1-yl radical, the 3-nitroimidazo[1,2-a]pyridin-8-yl radical, the 2-methyl-3-nitroimidazo[1,2-a]pyridin-8-yl radical, the 3-nitroimidazo[1,2-a]pyridin-yl radical, the 3-nitroimidazo[1,2-b]pyridazin-7-yl radical, and the 3-nitroimidazo[1,2-b]pyridazin-6-yl radical.

Suitable salts for compounds of the formula I, depending on substitution, include all acid addition salts or all salts with bases. Particular mention may be made of the pharmacologically acceptable salts of the organic and inorganic acids and bases that are commonly used in pharmacy. Suitable salts of this kind include, on the one hand, water-soluble and water-insoluble acid addition salts with acids such as, for example, hydrochloric acid, hydrobromic acid, phosphoric acid, nitric acid, sulfuric acid, acetic acid, citric acid. D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic add, stearic acid, toluenesulfonic acid, methanesulfonic acid or 3-hydroxy-2-naphthoic add, the adds being used in an equimolar proportion or in a proportion which deviates from equimolarity for preparing the salts, depending on whether the acid in question is monobasic or polybasic and on the particular salt desired.

On the other hand, salts with bases are also suitable. Examples of salts with bases that may be mentioned include alkali metal (lithium, sodium, potassium) or calcium, aluminum, magnesium, titanium, ammonium, meglumine or guanidinium salts, salt preparation here too being carried out using the bases in an equimolar proportion or in a proportion which deviates from equimolarity.

Pharmacologically unacceptable salts, which may be initially obtained, for example, during the preparation of the compounds of the invention on the industrial scale as process products, are converted into pharmacologically acceptable salts by methods known to the skilled worker.

The skilled worker is aware that the compounds of the invention and their salts, if isolated for example in crystalline form, may contain various amounts of solvents. The invention therefore further embraces all solvates and in particular all hydrates of the compounds of the formula I, and also all solvates and in particular all hydrates of the salts of the compounds of the formula I.

Selected compounds are those of the formula I
in which
R1 is hydrogen, 1–4C-alkyl or halogen,
R2 is hydrogen, 1–4C-alkyl or halogen,
R3 is hydrogen, 1–4C-alkyl or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, hydroxyl, 1–4C-alkyl, 1–4C-alkoxy, wholly or predominantly fluorine-substituted 1–4C-alkoxy or halogen,
R7 is a cyclic or bicyclic radical which is substituted by nitro and R9 and R10 and is selected from the group consisting of imidazole, imidazopyridazine and imidazopyridine,
A is 1–7C-alkylene.
B is a bond or 1–7C-alkylene,
X is O (oxygen), N-1–4C-alkyl, NH or $S(O)_n$ and
Y is CH or CR8,
where
R8 is hydroxyl, 1–4C-alkyl, 1–4C-alkoxy, wholly or predominantly fluorine-substituted 1–4C-alkoxy, trifluoromethyl or halogen,
R9 is hydrogen, 1–4C-alkyl, halogen, nitro, hydroxy-1–4C-alkyl or 1–4C-alkylcarbonyloxy-1–4C-alkyl,
R10 is hydrogen, 1–4C-alkyl or nitro, and
n is 0, 1 or 2,
and salts thereof, with the exception of those compounds in which X is $S(O)_n$ if at the same time 8 is a bond and A is 1-C-alkylene and the radicals -A-NR4—(R1)(R2)(R3)-pyrimidin-4-yl and —X—B—R7 are in position 3 (meta-position) to one another.

Particularly noteworthy selected compounds are those of the formula I
in which
R1 is hydrogen, 1–4C-alkyl or halogen,
R2 is hydrogen, 1–4C-alkyl or halogen,
R3 is hydrogen, 1–4C-alkyl or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, hydroxyl, 1–4C-alkyl, 1–4C-alkoxy, wholly or predominantly fluorine-substituted 1–4C-alkoxy or halogen,
R7 is a cyclic or bicyclic radical which is substituted by nitro and R9 and R10 and is selected from the group consisting of imidazole, imidazopyridazine and imidazopyridine,
A is 1–7C-alkylene,
B is a bond or 1–7C-alkylene,
X is O (oxygen), and
Y is CH or CR8,
where
R8 is hydroxyl, 1–4C-alkyl, 1–4C-alkoxy, wholly or predominantly fluorine-substituted 1–4C-alkoxy, trifluoromethyl or halogen.
R9 is hydrogen, 1–4C-alkyl, halogen, nitro, hydroxy-1–4C-alkyl or 1–4C-alkylcarbonyloxy-1–4C-alkyl, and
R10 is hydrogen, 1–4C-alkyl or nitro,
and salts thereof.

Compounds of the invention deserving of emphasis are those of the formula I in which
R1 is hydrogen, 1–4C-alkyl or halogen,
R2 is hydrogen, 1–4C-alkyl or halogen,
R3 is hydrogen or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, 1–4C-alkyl, 1–4CC-alkoxy or halogen,
R7 is a cyclic or bicyclic radical which is substituted by nitro and R9 and R10 and is selected from the group consisting of imidazole and imidazopyridazine,
A is methylene,
B is a bond or 1–4C-alkylene,
X is O (oxygen), NH or S(O), and
Y is CH or CR8,
where
R8 is hydrogen, hydroxyl, 1–4C-alkyl, 1–4C-alkoxy, wholly or predominantly fluorine-substituted 1–4C-alkoxy, trifluoromethyl or halogen,
R9 is hydrogen,
R10 is hydrogen,
n is 0,
and salts thereof.

Selected compounds of the invention deserving of emphasis are those of the formula I in which
R1 is hydrogen, 1–4C-alkyl or halogen,
R2 is hydrogen, 1–4C-alkyl or halogen, R3 is hydrogen or halogen, R4 is hydrogen or 1–4C-alkyl, R5 is hydrogen, hydroxyl, 1–4C-alkyl, 1–4C-alkoxy, wholly or predominantly fluorine-substituted 1–4C-alkoxy, trifluoromethyl or halogen, R6 is hydrogen, 0.1–4C-alkyl, 1–4C-alkoxy or halogen, R7 is a cyclic or bicyclic radical which is substituted by nitro and R9 and R10 and is selected from the group consisting of imidazole and imidazopyridazine, A is methylene, B is a bond or 1–4C-alkylene, X is O (oxygen), NH or $S(O)_n$ and Y is CH or CR8, where R8 is hydrogen, hydroxyl, 1–4C-alkyl, 1–4C-alkoxy, wholly or predominantly fluorine-substituted 1–4C-alkoxy, trifluoromethyl or halogen, R9 is hydrogen, R10 is hydrogen, n is 0.

and salts thereof, with the exception of those compounds in which X is S(O), if at the same time B is a bond and the radicals -A-NR4—(R1)(R2)(R3)-pyrimidin-4-yl and —X—B—R7 are in position 3 (meta-position) to one another.

Particularly noteworthy selected compounds of the invention deserving of emphasis are those of the formula I in which R1 is hydrogen, 1–4C-alkyl or halogen, R2 is hydrogen, 1–4C-alkyl or halogen, R3 is hydrogen or halogen, R4 is hydrogen or 1–4C-alkyl, R5 is hydrogen, hydroxyl, 1–4C-alkyl, 1–4C-alkoxy, wholly or predominantly fluorine-substituted 1–4C-alkoxy, trifluoromethyl or halogen, R6 is hydrogen, 1–4C-alkyl, 1–4C-alkoxy or halogen, R7 is a cyclic or bicyclic radical which is substituted by nitro and R9 and R10 and is selected from the group consisting of imidazole and imidazopyridazine, A is methylene, B is a bond or 1–4C-alkylene, X is O (oxygen), and Y is CH or CR8, where R8 is hydrogen, hydroxyl, 1–4CC-alkyl, 1-4-C-alkoxy, wholly or predominantly fluorine-substituted 1–4C-alkoxy, trifluoromethyl or halogen, R9 is hydrogen, and R10 is hydrogen, and salts thereof.

One embodiment of the compounds deserving of emphasis (embodiment a) are those of the formula I in which B is a bond and R7 is an imidazopyridazine radical substituted by nitro and the radicals R9 and R10.

Selected compounds of embodiment a are those in which X is O (oxygen) or NH.

A further embodiment of the compounds deserving of emphasis (embodiment b) are those of the formula I in which B is an ethylene radical and R7 is an imidazole radical substituted by nitro and the radicals R9 and R10.

Compounds of the invention deserving of particular emphasis are those of the formula I in which R1 is hydrogen or methyl, R2 is hydrogen or methyl, R3 is hydrogen or chlorine, R4 is hydrogen or methyl.

R5 is hydrogen, 1–4C-alkyl, 1–4C-alkoxy, wholly or predominantly fluorine-substituted 1-4-alkoxy, trifluoromethyl or halogen, R6 is hydrogen, 1–4C-alkyl, 1–4C-alkoxy or halogen, R7 is a 3-nitroimidazo[1,2-b]pyridazin-6-yl radical or a 2-methyl-5-nitroimidazol-1-yl radical, A is methylene, B is a bond or 1-2C-alkylene, X is O (oxygen), NH or S, and Y is CH, and salts thereof.

Selected compounds of the invention deserving of particular emphasis are those of the formula I in which R1 is hydrogen or methyl, R2 is hydrogen or methyl, R3 is hydrogen or chlorine, R4 is hydrogen or methyl, R5 is hydrogen, 1–4C-alkyl, 1–4C-alkoxy, wholly or predominantly fluorine-substituted 1–4C-alkoxy, trifluoromethyl or halogen, R6 is hydrogen, 1–4C-alkyl, 1–4C-alkoxy or halogen, R7 is a 3-nitroimidazo[1,2-b]pyridazin-6-yl radical or a 2-methyl-5-nitroimidazol-1-yl radical, A is methylene, B is a bond or 1-2C-alkylene, X is O (oxygen), NH or S, and Y is CH, and salts thereof, with the exception of those compounds in which X is S if at the same time B is a bond and the radicals -A-NR4—(R1)(R2)(R3)-pyrimidin-4-yl and —X—B—R7 are in position 3 (meta-position) to one another.

Particularly noteworthy selected compounds of the invention deserving of emphasis are those of the formula I in which R1 is hydrogen or methyl, R2 is hydrogen or methyl, R3 is hydrogen or chlorine, R4 is hydrogen or methyl R5 is hydrogen, 1–4C-alkyl, 1–4C-alkoxy, wholly or predominantly fluorine-substituted 1–4C-alkoxy, trifluoromethyl or halogen, R6 is hydrogen, 1–4C-alkyl, 1–4C-alkoxy or halogen, R7 is a 3-nitroimidazo[1,2-b]pyridazin-6-yl radical or a 2-methyl-5-nitroimidazol-1-yl radical, A is methylene, B is a bond or 1-2C-alkylene, X is O (oxygen), and Y is CH, and salts thereof.

Preferred compounds of embodiment a are those in formula I*

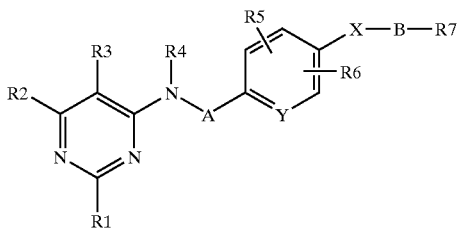

(I*)

in which
R1 is hydrogen or methyl,
R2 is hydrogen or methyl,
R3 is hydrogen or chlorine,
R4 is hydrogen or methyl,
R5 is hydrogen, hydroxyl, methyl, methoxy, ethoxy, cyclopropylmethoxy, isobutoxy, trifluoromethoxy, difluoromethoxy, trifluoromethyl or chlorine.
R6 is hydrogen, methyl, methoxy or chlorine,
R7 is a 3-nitroimidazo[1,2-b]pyridazin-6-yl radical,
A is methylene,
B is a bond,
X is O (oxygen), NH or S, and
Y is CH,
and salts thereof.

Preferred compounds of embodiment b are those in formula I* in which
R1 is hydrogen or methyl,
R2 is hydrogen or methyl,
R3 is hydrogen or chlorine,
R4 is hydrogen or methyl,
R5 is hydrogen, hydroxyl, methyl, methoxy, ethoxy, cyclopropylmethoxy, isobutoxy, trifluoromethoxy, difluoromethoxy, trifluoromethyl or chlorine,
R6 is hydrogen, methyl, methoxy or chlorine,
R7 is a 2-methyl-5-nitroimidazo-1-yl radical,
A is methylene,
B is ethylene,
X is O (oxygen), NH or S, and
Y is CH,
and salts thereof.

Particularly preferred compounds of embodiment a are those in formula I* in which
R1 is methyl,
R2 is methyl,
R3 is chlorine,
R4 is hydrogen,
R5 is hydrogen,
R6 is hydrogen,
R7 is a 3-nitroimidazo[1,2-b]pyridazin-6-yl radical,
A is methylene,
B is a bond,
X is O (oxygen), and
Y is CH,
and salts thereof.

Particularly preferred compounds of embodiment b are those in formula I* in which
R1 is methyl,
R2 is methyl,
R3 is chlorine,
R4 is hydrogen,
R5 is hydrogen,
R6 is hydrogen,
R7 is a 2-methyl-5-nitroimidazo-1-yl radical,
A is methylene,
B is ethylene,
X is O (oxygen), and
Y is CH,
and salts thereof.

One aspect in accordance with the invention and deserving of particular emphasis comprises compounds of the formula I characterized by the formula I**

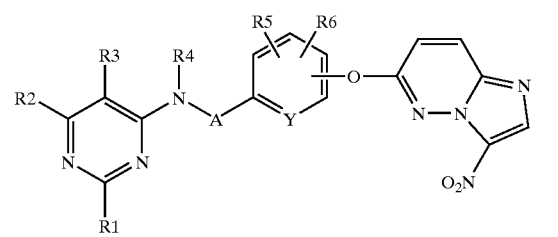

(I**)

in which
R1 is hydrogen, 1–4C-alkyl or halogen,
R2 is hydrogen, 1–4C-alkyl or halogen.
R3 is hydrogen or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, 1–4C-alkyl, 1–4C-alkoxy or halogen,
A is methylene,
Y is CH or CR8,
where
R8 is hydrogen, hydroxyl, 1–4C-alkyl, 1–4C-alkoxy, wholly or predominantly fluorine-substituted 1–4C-alkoxy, trifluoromethyl or halogen,
and salts thereof.

Compounds of the invention of the formula I** deserving of emphasis are those in which
R1 is hydrogen or methyl,
R2 is hydrogen or methyl,
R3 is hydrogen or chlorine,
R4 is hydrogen or methyl,
R5 is hydrogen, hydroxy, 1–4C-alkyl, 1–4C-alkoxy, wholly or predominantly fluorine-substituted 1–4C-alkoxy or halogen,
R6 is hydrogen, 1–4C-alkyl, 1–4C-alkoxy or halogen,
A is methylene, and
Y is CH,
and salts thereof.

Compounds of the invention of the formula I** deserving of particular emphasis are those in which
R1 is methyl,
R2 is methyl,
R3 is chlorine,
R4 is hydrogen, R5 is hydrogen, hydroxy, 1–4C-alkyl, 1–4C-alkoxy, wholly or predominantly fluorine-substituted 1–4C-alkoxy or halogen, R5 is hydrogen or 1–4C-alkoxy, A is methylene, and A is CH, and salts thereof.

Selected compounds of the invention of the formula I** deserving of particular emphasis are those in which R1 is methyl, R2 is methyl, R3 is chlorine, R4 is hydrogen, R5 is hydrogen, hydroxylmethyl, methoxy, ethoxy, isobutoxy (2-methyl-1-propoxy), cyclopropylmethoxy, 2,2,2-trifluoroethoxy, difluoromethoxy, fluorine chlorine or bromine, R6 is hydrogen or methoxy, A is methylene, and Y is CH, and salts thereof.

Compounds of the invention of the formula I** that may be mentioned by way of example are:

(5-chloro-2,6-dimethylpyrimidin-4-yl)[2-(3-nitroimidazo[1,2-b]pyridazin-6-yloxy)benzyl]amine, (5-chloro-2,6-dimethylpyrimidin-4-yl)[4-methoxy-2-(3-nitroimidazo[1,2-b]pyridazin-6-yloxy)benzyl]amine, (5-chloro-2,6-dimethylpyrimidin-4-yl)[3-ethoxy-4-(3-nitroimidazo[1,2-b]pyridazin-6-yloxy)benzyl]amine, (5-chloro-2,6-dimethylpyrimidin-4-yl)[5-bromo-3-methoxy-4-(3-nitroimidazo[1,2-b]pyridazin-6-yloxy)-benzyl]amine, (5-chloro-2,6-dimethylpyrimidin-4-yl)[5-chloro-3-methoxy-4-(3-nitroimidazo[1,2-b]pyridazin-6-yloxy)-benzyl]amine.

(5-chloro-2,6-dimethylpyrimidin-4-yl)[3,4-dimethoxy-5-(3-nitroimidazo[1,2-b]pyridazin-6-yloxy)benzyl]-amine, (5-chloro-2,6-dimethylpyrimidin-4-yl)[2-fluoro-4-(3-nitroimidazo[1,2-b]pyridazin-6-yloxy)benzyl]amine, (5-chloro-2.6-dimethylpyrimidin-4-yl)[3-fluoro-4-(3-nitroimidazo[1,2-b]pyridazin-6-yloxy)benzyl]amine, (5-chloro-2,6-dimethylpyrimidin-4-yl)[3-fluoro-4-(3-nitroimidazo[1,2-b]pyridazin-6-yloxy)benzyl]amine, (5-chloro-2,6-dimethylpyrimidin-4-yl)[3-methoxy-4-(3-nitroimidazo[1,2-b]pyridazin-6-yloxy)benzyl]-amine, (5-chloro-2,6-dimethylpyrimidin-4-yl)[3-(2,2,2-trifluoroethoxy)-4-(3-nitroimidazo[1,2-b]pyridazin-6-yloxy)-benzyl]amine, (5-chloro-2,6-dimethylpyrimidin-4-yl)[3-[3-(2-methylpropoxy)-4-(3-nitroimidazo[1,2-b]pyridazin-6-yloxy)benzyl]amine, (5-chloro-2,6-dimethylpyrimidin-4-yl)[3-hydroxy-4-(3-nitroimidazo[1,2-b]pyridazin-6-yloxy)benzyl]amine, (5-chloro-2,6-dimethylpyrimidin-4-yl)[4-hydroxy-3-(3-nitroimidazo[1,2-b]pyridazin-6-yloxy)benzyl]amine, and the salts of these compounds.

The compounds of the formula I according to the invention may be synthesized in a variety of ways. In principle the compounds of the formula I may be prepared in conventional manner by reacting the compounds of the formula II with the compounds of the formula III (in which L is an eliminable group, e.g., a halogen atom, especially chlorine, or a mesyloxy group).

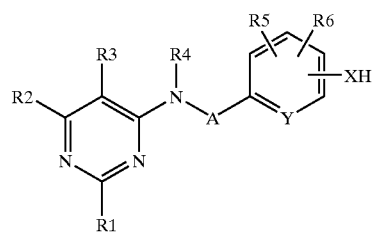

L—B—R7   (III)

The reaction of the compounds of the formula II with the compounds of the formula III takes place, for example, as described by way of example in the section "Examples", preferably in inert anhydrous solvents (such as dimethylformamide, for example) in the presence of an organic or, preferably, inorganic auxiliary base (such as potassium carbonate, for example).

The compounds of the formulae II and III are known or may be prepared as described in the examples below under "Starting compounds" or in analogy thereto from corresponding known compounds in conventional manner using customary process steps.

The examples which follow illustrate the invention without restricting it. The compounds of the invention and the starting compounds may be prepared in a manner analogous to that described in the examples. The abbreviation m.p. denotes melting point, conc. stands for "concentrated", h stands for hour(s), and min for minute(s). The compounds named as end products and the salts of these compounds are a particularly preferred subject matter of the invention.

EXAMPLES

End Products 1. (5-Chloro-2,6-dimethylpyrimidin-4-yl)[4-(3-nitroimidazo[1,2-b]pyridazin-6-yloxy)benzyl]amine 8.0 g (30 mmol) of 4-[(5-chloro-2,6-dimethylpyrimidin-4-ylamino)methyl]phenol, 6.0 g (30 mmol) of 6-chloro-3-nitroimidazo[1,2-b]pyridazine and 20.7 g (150 mmol) of potassium carbonate in 150 ml of anhydrous dimethylformamide are heated at 80° C. with vigorous stirring for 1 h. After cooling to room temperature, the mixture is poured into water (1 l) and extracted with ethyl acetate (3×500 ml). The combined organic extracts are washed with water (500 ml), dried over sodium sulfate and concentrated. The beige solid (12.5 g) remaining is purified by chromatography on silica gel (mobile phase: toluene/acetone=2:1). The fractions with Rf=0.4 are collected and concentrated. The residue is suspended in 100 ml of methanol and the suspension is stirred for 30 min. Following filtration, this operation is repeated. After drying in a vacuum drying cabinet at 40° C., 7.8 g (61%) of the title compound are isolated as an almost white powder. m.p.: 203° C.

2. 5-chloro-2,6-dimethyl-4-[4-(3-nitroimidazo[1,2-b]pyridazin-6-yloxy)benzylamino]pyrimidin-1-lum methanesulfonate 1.0 g (2.30 mmol) of (5-chloro-2,6-dimethylpyrimidin-4-yl)[4-(3-nitroimidazo[1,2-b]pyridazin-6-yloxy)-benzyl]amine (from example 1) are dissolved in 90 ml of boiling acetone, and 230 mg (2.36 mmol) of 90% strength methanesulfonic acid are added. After slow cooling to room temperature, the mixture is stirred at 4° C. for 30 minutes. After filtration, washing of the precipitate with cold acetone and drying at 40° C. in a vacuum drying cabinet, 0.88 g (73%) of the title compound is isolated as a colorless crystallizate. m.p.: 208° C.

3. (5-Chloro-2,6-dimethylpyrimidin-4-yl)[3-(3-nitroimidazo[1,2-b]pyridazin-6-yloxy)benzyl]-amine In analogy to the method described in example 1, 7.9 g (30 mmol) of 3-[(5-chloro-2,6-dimethylpyrimidin-4-ylamino)methyl]phenol (from example B2), 6.08 g (30 mmol) of 6-chloro-3-nitroimidazo-[1,2-b]pyridazine and 20.9 g (150 mmol) of potassium carbonate are reacted in 125 ml of dimethylformamide. After chromatography on silica gel (mobile phase: gradient toluene/dioxane 5:1 to 2:1) and crystallization from methylene chloride/methanol and extraction with stirring from diisopropyl ether, 10.95 g (85%) of the title compound are isolated as a pale beige solid. m.p.: 222–223° C.

4. (5-Chloro-2,6-dimethylpyrimidin-4-yl)[3-methoxy-4-(3-nitroimidazo[1,2-b]pyridazin-6-yloxy)-benzyl]amine In analogy to the method described in example 1, 1.25 g (4.25 mmol) of 4-[(5-chloro-2,6-dimethyl-pyrimidin-4-ylamino)methyl]-2-methoxyphenol (from example B3), 0.86 g (4.25 mmol) of 6-chloro-3-nitroimidazo[1,2-b]pyridazine and 3.0 g (21.25 mmol) of potassium carbonate are reacted in 25 ml of dimethylformamide. After chromatography on silica gel (mobile phase: gradient toluene/dioxane 5:1 to 2:1) and crystallization from methylene chloride/methanol, 1.24 g (64%) of the title compound are isolated as a pale beige solid. m.p.: 229–232° C.

5. (5-Chloro-2,6-dimethylpyrimidin-4-yl)[4-methoxy-3-nitroimidazo[1,2-b]pyridazin-6-yloxy)-benzyl]amino In analogy to the method described in example 1, 1.5 g (5.1 mmol) of 5-[(5-chloro-2,6-dimethyl-pyrimidin-4-ylamino)methyl]-2-methoxyphenol (from example B4), 1.03 g (5.1 mmol) of 6-chloro-3-nitro-imidazo[1,2-b]pyridazine and 3.56 g (25.5 mmol) of potassium carbonate are reacted in 25 ml of dimethylformamide. After crystallization of the crude product from isopropanol, 1.68 g (72%) of the title compound are isolated as a pale beige solid. m.p.: 273–274° C.

6. (5-Chloro-2,6-dimethylpyrimidin-4-yl)[3-cyclopropylmethoxy-4-(3-nitroimidazo[1,2-b]pyridazin-6-yloxy)benzyl]amine In analogy to the method described in example 1, 540 mg (1.6 mmol) of 4-[(5-chloro-2,6-dimethyl-pyrimidin-4-ylamino)methyl]-2-cyclopropylmethoxyphenyl (from example B5), 321 mg (1.6 mmol) of 6-chloro-3-nitrolmidazo[1,2-b]pyridazine and 450 mg (3.2 mmol) or potassium carbonate are reacted in 10 ml of dimethylformamide. After crystallization of the crude product from methanol, 620 mg (78%) of the title compound are isolated as a pale beige solid. m.p.: 178–180° C.

7. (3-Cyclopropylmethoxy-4-(3-nitroimidazo[1,2-b]pyridazin-6-yloxy)benzyl]-2,6-dimethyl-pyrimidin-4-yl)amine In analogy to the method described in example 1, 1.5 g (4.7 mmol) of 2-cyclopropylmethoxy-4-[(2,6-dimethylpyrimidin-4-ylamino)methyl]phenyl (from example B6), 840 mg (4.2 mmol) of 6-chloro-3-nitroimidazo[1,2-b]pyridazine and 3.2 g (23.5 mmol) of potassium carbonate are reacted in 25 ml of dimethylformamide. Alter chromatography on silica gel (mobile phase: toluene/dioxane/ammonia=2:1:0.05) and subsequent crystallization from methanol, 420 mg (20%) of the title compound are isolated as a pale beige solid. m.p.: 113–118° C.

8. (5-Chloro-2,6-dimethylpyrimidin-4-yl)[3-(1,1-difluoromethoxy)-4-(3-nitroimidazo[1,2-b]pyridazin-6-yloxy)benzyl]amine In analogy to the method described in example 1, 2.0 g (6 mmol) of 4-[(5-chloro-2,8-dimethylpyrimidin-4-ylamino) methyl]-2-(1,1-difluoromethoxy)phenol (from example B7), 1.22 g (6 mmol) of 6-chloro-3-nitroimidazo[1,2-b]pyridazine and 4.2 g (30 mmol) of potassium carbonate are reacted in 50 ml of dimethylformamide. After crystallization from methanol, 1.97 g (67%) of the title compound are isolated as a pale beige solid. m.p.: 191–193.5° C.

In analogy to the method described for the above examples, the following compounds are prepared as well:

9. (5-Chloro-2,6-dimethylpyrimidin-4-yl)[3-methyl-4-(3-nitroimidazo[1,2-b]pyridazin-6-yloxy)-benzyl]amine (m.p.: 183–185° C.)

10. (5-Chloro-2,6-dimethylpyrimidin-4-yl)[3-fluoro-4-(3-nitroimidazo[1,2-b]pyridazin-6-yloxy)-benzyl]amine (m.p.: 193–196° C.)

11. (5-Chloro-2,6-dimethylpyrimidin-4-yl)[2-fluoro-4-(3-nitroimidazo[1,2-b]pyridazin-6-yloxy)-benzyl]amine (m.p.: 147–149° C.)

12. (5-Chloro-2,6-dimethylpyrimidin-4-yl)[4-(3-nitroimidazo[1,2-b]pyridazin-6-yloxy)-3-(2,2,2-trifluoroethoxy)benzyl]amine (m.p.: 185–188° C.)

13. (5-Chloro-2,6-dimethylpyrimidin-4-yl)[3-methoxy-5-(3-nitroimidazo[1,2-b]pyridazin-6-yloxy)-benzyl]amine (m.p.: 198–199° C.)

14. 3-[(5-Chloro-2,6-dimethylpyrimidin-4-ylamino)methyl]-5-(3-nitroimidazo[1,2-b]pyridazin-6-yloxy)phenol (m.p.: 263° C.)

15. (5-Chloro-2,6-dimethylpyrimidin-4-yl)[2-fluoro-5-(3-nitroimidazo[1,2-b]pyridazin-6-yloxy)-benzyl]amine (m.p.: 168–167° C.)

16. [3-Bromo-5-methoxy-4-(3-nitroimidazo[1,2-b]pyridazin-6-yloxy)benzyl](5-chloro-2,6-dimethyl-pyrimidin-4-yl)amine (m.p.: 230–234° C.)

17. (5-Chloro-pyrimidin-4-yl)-[4-(3-nitro-imidazo[1,2-b]pyridazin-6-yloxy)-benzyl]-amine 0.18 g (3.6 mmol) of 6-chloro-3-nitro-imidazo[1,2-b]pyridazine are added to a solution of 0.85 g (3.6 mmol) of 4-[(5-chloro-pyrimidin-4-ylamino)-methyl]-phenol (from example A14) and 2.5 g (18 mmol) of potassium carbonate in 10 ml of dry N,N-dimethylformamide and the reaction mixture is stirred at 80° C. for 3 h. The temperature is allowed to raise to room temperature and the mixture is poured into water (100 ml). The precipitate is filtered off and purified by silica gel chromatography (toluene/dioxane=2:1) to yield 1.1 g (78%) of the title compound as a beige powder of m.p. 185° C.

18. (5-Chloro-2,6-dimethyl-pyrimidin-4-yl)-[4-(3-nitro-imidazo[1,2-b]pyridazin-6-yloxy)-5-hydroxy-benzyl]-amine 0.14 g (1.0 mmol) of dimedone and catalytic amount of tetrakis(triphenylphosphine)palladium(0) (12 mg) are added to a solution of 0.48 g (1.0 mmol) of [3-allyloxy-4-(3-nitro-imidazo[1,2-b]pyridazin-6-yloxy)-benzyl]-(5-chloro-2,6-dimethyl-pyrimidin-4-yl)-amine (from example A15) in 15 ml of dry toluene. The reaction mixture is refluxed under nitrogen for 1 h and then cooled to room temperature. The solution is poured into water (100 ml), extracted with ethyl acetate (4×100 ml) and the combined organic layers are dried with magnesium sulphate and concentrated in vacuo. The residue is crystallized from petroleum ether to give 0.44 g (50%) of the title compound as a beige powder of m.p. >114° C.

Starting Compounds

A1. (4-Benzyloxybenzyl)(5-chloro-2,6-dimethylpyrimidin-4-yl)amine hydrochloride

A solution of 73.4 g (0.465 mol) of 4-amino-5-chloro-2,6-dimethylpyrimidine in 370 ml of anhydrous N-methylpyrrolidone is added dropwise over 45 min under a nitrogen atmosphere at room temperature to a suspension of 19.5 g (0.49 mol) of sodium hydride (60% suspension in liquid paraffin) in 80 ml of anhydrous N-methylpyrrolidone. The mixture is stirred at room temperature for 1 h and then cooled to 4° C. Then a solution of 111.0 g (0.465 mol) of 4-benzyloxybenzyl chloride in anhydrous N-methylpyrrolidone is added dropwise, with vigorous stirring, at a rate such that the internal temperature does not rise higher than 5° C. (about 1 h). Thereafter, the mixture is warmed to room temperature and stirred for 1 h. The solution is subsequently poured into 4 l of water and extracted with ethyl acetate (3×1 l). The combined organic extracts are washed with water (2 l), dried over sodium sulfate and concentrated. The oil (180 g) which remains is dissolved in 400 ml of isopropanol and is admixed dropwise with stirring with 100 ml of saturated ethereal hydrochloric acid. Thereafter, further ethyl acetate is added and the mixture is stirred at room temperature for 1 h for complete precipitation of the hydrochloride. The precipitate is filtered off with suction, washed with ethyl acetate (500 ml) and dried in a vacuum drying cabinet at 40° C. 114.8 g (63%) of the title compound are isolated as a beige solid. m.p.: 227° C.

A2. (3-Benzyloxybenzyl)(5-Chloro-2,6-dimethylpyrimidin-4-yl)amino

In analogy to the method described in example A1, 19.3 g (0.12 mol) of 4-amino-5-chloro-2,6-dimethyl-pyrimidine, 28.3 g (0.12 mol) of 3-benzyloxybenzyl chloride and 5.2 g (0.13 mol) of sodium hydride (60% suspension in liquid paraffin) are reacted in a total of 170 ml of N-methylpyrrolidone. After chromatography on silica gel (mobile phase: toluene/dioxane=20:1), the title compound is isolated as an amorphous solid. Yield: 23.8 g (56% of theory). $^1$H NMR spectrum (CDCl$_3$, δ ppm): 7.4-7.1 (m, 6H), 7.0–6.8 (m, 3H), 5.56 (tb, NH), 5.05 (s, 2H), 4.67 (d, 2H), 2.49 (s, 3H), 2.41 (s, 3H)

A3. (4-Benzyloxy-3-methoxybenzyl)(5-chloro-2,6-dimethylpyrimidin-4-yl)amine

In analogy to the method described in example A1, 3.67 g (22.8 mmol) of 4-amino-5-chloro-2,6-dimethylpyrimidine, 6.0 g (22.8 mmol) of 4-benzyloxy-3-methoxybenzyl chloride and 0.91 g (23 mmol) of sodium hydride (60% suspension in liquid paraffin) are reacted in a total of 190 ml of N-methylpyrrolidone. After chromatography on silica gel (mobile phase: toluene/dioxane=10:1) and crystallization from petroleum ether, the title compound is isolated as a pale beige solid. Yield: 3.42 g (39% of theory). m.p.: 101–105° C.

A4. (3-Benzyloxy-4-methoxybenzyl)(5-chloro-2,6-dimethylpyrimidin-4-yl)amine

In analogy to the method described in example A1, 6.11 g (38 mmol) of 4-amino-5-chloro-2,6-dimethylpyrimidine, 10.5 g (40 mmol) of 3-benzyloxy-4-methoxybenzyl chloride and 1.52 g (38 mmol) of sodium hydride (60% suspension in liquid paraffin) are reacted in a total of 225 ml of N-methylpyrrolidone. After chromatography on silica gel (mobile phase: toluene/dioxane=10:1) and crystallization from petroleum ether, the title compound is isolated as a pale beige solid. Yield: 5.2 g (36% of theory). m.p.: 111–117° C.

A5. (4-Benzyloxy-3-cyclopropylmethoxybenzyl)(5-chloro-2,6-dimethylpyrimidin-4-yl)amine A suspension of 3.0 g (19 mmol) of 4-amino-5-chloro-2,8-dimethylpyrimidine and 2.4 g (20.9 mmol) of potassium tert-butoxide in 15 ml of tert-butanol is stirred at room temperature under a nitrogen atmosphere for 2 h and then heated to 60° C. A solution of 5.75 g (19 mmol) of 4-benzyloxy-3-cyclopropylmethoxybenzyl chloride in 15 ml of toluene is then added dropwise and the mixture is stirred at 60° C. for 1 h. After cooling to room temperature, the mixture is poured into water (100 ml) and extracted with ethyl acetate (2×50 ml). The combined organic extracts are then washed in succession with 2N acetic acid (2×30 ml), water (30 ml) and sodium bicarbonate solution (30 ml), dried over magnesium sulfate and concentrated. After crystallization of the residue from diisopropyl ether, 5.8 g (72%) of the title compound are isolated as a pale beige solid. m.p.: 137–138° C.

A6. [4-Benzyloxy-3-(1,1-difluoromethoxy)benzyl](5-chloro-2,6-dimethylpyrimidin-4-yl)amine In analogy to the method described in example A5, 3.8 g (22.7 mmol) of 4-amino-5-chloro-2,6-dimethylpyrimidine, 2.8 g (25 mmol) of potassium tert-butoxide and 6.8 g (22.7 mmol) of 4-benzyloxy-3-(1,1-difluoromethoxy)benzyl chloride are reacted in 15 ml of tert-butanol and 15 ml of toluene and the product is worked up. After chromatography on silica gel (mobile phase: toluene/dioxane=5:1), the title compound is obtained as a viscous, colorless oil. $^1$H NMR spectrum (CDCl$_3$, δ ppm): 7.5-7.3 (m, 5H), 7.19 (m, 1H), 7.12 (dd, 1H), 6.58 (t, 1H, J=80 Hz), 5.58 (tb, NH), 5.13 (s, 2H), 4.63 (d, 2H), 2.51 (s, 3H), 2.43 (s, 3H)

In analogy to the method described in example A5, the following compounds are prepared:

A7. (5-Chloro-2,6-dimethylpyrimidin-4-yl)(4-methoxy-3-methylbenzyl)amine (m.p.: 85–88° C.)

A8. (5-Chloro-2,6-dimethylpyrimidin-4-yl)(3-fluoro-4-methoxybenzyl)amino (m.p.: 125–126° C.)

A9. [4-Benzyloxy-3-(2,2,2-trifluoroethoxy)benzyl](5-chloro-2,6-dimethylpyrimidin-4-yl)amine (m.p.: 82–84° C.)

A10. [4-Benzyloxy-3-bromo-5-methoxybenzyl](5-chloro-2,6-dimethylpyrimidin-4-yl)amine $^1$H-NMR (CDCl$_3$, δ ppm): 7.55-7.5 (m, 2H), 7.4–7.3 (m. 3H), 7.11 (m, 1H), 6.88 (m, 1H), 5.59 (t, NH), 5.01 (s, 2H), 4.62 (d, 2H), 3.81 (s, 3H), 2.50 (s, 3H), 2.41 (s, 3H)

A11. (5-Chloro-2,6-dimethylpyrimidin-4-yl)(3,5-dimethoxybenzyl)amine $^1$H-NMR (CDCl$_3$, δ ppm): 6.5 (m, 2H), 6.38 (m, 1H), 5.55 (t, NH), 4.65 (d, 2H), 3.80 (s, 6H), 2.50 (s, 3H), 2.42 (s, 3H)

A12. (5-Chloro-2,6-dimethylpyrimidin-4-yl)(2-fluoro-4-methoxybenzyl)amine $^1$H-NMR (CDCl$_3$, δ ppm): 7.3 (t, 1H), 6.7–6.5 (m, 2H), 5.58 (t, NH), 4.68 (d, 2H), 3.81 (s, 3H), 2.51 (s, 3H), 2.43 (s, 3H)

A13. (5-Chloro-2,6-dimethylpyrimidin-4-yl)(2-fluoro-5-methoxybenzyl)amine $^1$H-NMR (CDCl$_3$, δ ppm): 7.1-6.9 (m, 2H), 6.75 (m, 1H), 5.6 (t, NH), 4.72 (d, 2H), 3.81 (s, 3H), 2.52 (s, 3H), 2.41 (s, 3H)

A14. 4-[(5-Chloro-pyrimidin-4-ylamino)-methyl]-phenol

A solution of 0.8 g (2.4 mmol) of (4-benzyloxy-benzyl)-(5-Chloro-pyrimidin-4-yl)-amine (from example B10) in dry methanol (20 ml) is treated with 2.2 ml (24.2 mmol) of cyclohexadiene, 40 μl (5% mmol) of HCl and a catalytic amount of palladium on coal (79 mg). The reaction mixture is refluxed for 4 h, the solution cooled to room temperature and the solvent evaporated in vacuo. The residue is purified by chromatography on silica gel (toluene/dioxane=1:1+0.5% Ammonia) to yield 0.9 g (61%) of the title compound as a beige powder of m.p. 190°–191° C.

A15. [3-Allyloxy-4-(3-nitro-imidazo[1,2-b]pyridazin-6-yloxy)-benzyl]-(5-Chloro-2,6-dimethyl-pirimidin-4-yl)-amino 2.7 g (8.5 mmol) of 2-allyloxy-4-[(5-Chloro-2,6-dimethyl-pyrimidin-4-ylamino)-methyl]-phenol (from example B11), 1.7 g (8.5 mmol) of 6-chloro-3-nitro-imidazo

[1,2-b]pyridazine and 5.9 g (42.5 mmol) of potassium carbonate are suspended in dry N,N-dimethylformamide (85 ml) and the temperature is kept at 80° C. After stirring for 2 h, the reaction mixture is cooled to room temperature and poured into water (800 ml). The precipitate is filtered off and dried in vacuo to yield 4.1 g (97%) of the title compound as a beige powder of m.p. 135°–138° C.

B1. 4-[(5-Chloro-2,6-dimethylpyrimidin-4-ylamino) methyl]phenol 112 g (0.286 mol) of (4-benzyloxybenzyl)(5-Chloro-2,6-dimethylpyrimidin-4-yl)amine hydrochloride (from example A1) are suspended in ethanol (1.1 l) and 12.5 N hydrochloric acid (1.1 l) and the suspension is heated at reflux for 1 h. The yellow solution is cooled to room temperature and stirred into ice-water (4 l). The solution is then adjusted to a pH of 8 using 10 N sodium hydroxide solution and extracted with ethyl acetate (3×1 l). The combined organic extracts are washed with water (1 l), dried over sodium sulfate and concentrated to a volume of about 100 ml. The residue is taken up in ethyl acetate (100 ml) and diisopropyl ether (200 ml) and stirred at room temperature for 15 min. The crystals are filtered and washed with diisopropyl ether/ethyl acetate) (2:1). Drying in a vacuum drying cabinet at 40° C. gives 38.4 g (51%) of the title compound as a pale beige solid. m.p.: 202° C.

B2. 3-[(5-Chloro-2,6-dimethylpyrimidin-4-ylamino) methyl]phenol

In analogy to the method described in example B1, 23.5 g (66 mmol) of (3-benzyloxybenzyl)(5-chloro-2,6-dimethylpyrimidin-4-yl)amine (from example A2) are reacted with 240 ml of 12.5N hydrochloric acid in 240 ml of ethanol. Extraction with ethyl acetate at a pH of 8 gives, after concentration, a solid residue which is extracted by stirring with water and dried. 9.03 g (52%) of the title compound are isolated as a beige crystallizate. m.p.: 194–197° C.

B3. 4-[(5-Chloro-2,6-dimethylpyrimidin-4-ylamino) methyl]-2-methoxyphenol

In analogy to the method described in example B1, 3.0 g (7.8 mmol) of (4-benzyloxy-3-methoxy-benzyl)(5-chloro-2, 6-dimethylpyrimidin-4-yl)amine (from example A3) are reacted with 30 ml of 12.5N hydrochloric acid in 30 ml of ethanol. Extraction with ethyl acetate at a pH of 8 gives, after concentration, a solid residue which is chromatographed on silica gel (mobile phase: toluene/dioxane=5:1). Crystallization with toluene gives 1.38 g (60%) of the title compound as a beige crystallizate. m.p.: 179–181.5° C.

B4. 5-[(5-Chloro-2,6-dimethylpyrimidin-4-ylamino) methyl]-2-methoxyphenol

In analogy to the method described in example B1, 3.0 g (7.8 mmol) of (3-benzyloxy-4-methoxy-benzyl)(5-chloro-2, 6-dimethylpyrimidin-4-yl)amine (from example A4) are reacted with 30 ml of 12.5N hydrochloric acid in 30 ml of ethanol. Extraction with ethyl acetate at a pH of 8 gives, after concentration, a solid residue which is chromatographed on silica gel (mobile phase: toluene/dioxane=5:1). Crystallization from toluene/methanol gives 1.86 g (72%) of the title compound as a beige crystallizate. m.p.: 165–168° C.

B5. 4-[(5-Chloro-2,6-dimethylpyrimidin-4-ylamino) methyl]-2-cyclopropylmethoxyphenol A solution of 2.0 g (4.7 mmol) of (4-benzyloxy-3-cyclopropylmethoxybenzyl)(5-chloro-2,6-dimethyl-pyrimidin-4-yl)amine (from example A5) in 50 ml of methanol and 20 ml of glacial acetic acid is admixed with 250 mg of Pd-on-carbon catalyst (type 38H, Johnson Matthey) and hydrogenated by circulation with hydrogen until about 1 equivalent of hydrogen (about 190 ml) has been taken up. After filtration to remove the catalyst, the solution is concentrated and the residue is chromatographed on silica gel (mobile phase: toluene/dioxane/ammonia=2:1:0.05). The fractions with Rf=0.35 are collected and concentrated. After crystallization from diisopropyl ether, 550 mg (35%) of the title compound are isolated as a beige powder. m.p.: 123–125° C.

B6. 2-Cyclopropylmethoxy-4-[(2,6-dimethylpyrimidin-4-ylamino)methyl]phenol

A solution of 2.0 g (4.7 mmol) of (4-benzyloxy-3-cyclopropylmethoxybenzyl)(5-chloro-2,6-dimethyl-pyrimidin-4-yl)amine (from example A5) in 50 ml of methanol and 20 ml of glacial acetic acid is admixed with 250 mg of Pd-on-carbon catalyst (type 38H, Johnson Matthey) and hydrogenated by circulation with hydrogen until about 2 equivalents of hydrogen (about 350 ml) have been taken up. After filtration to remove the catalyst, the solution is concentrated and the residue is chromatographed on silica gel (mobile phase: toluene/dioxane/ammonia=2:1:0.05). The fractions with Rf=0.15 are collected and concentrated. The residue (1.5 g), which is of poor solubility, is reacted further without additional purification (see example 7).

B7. 4-[(5-Chloro-2,5-dimethylpyrimidin-4-ylamino) methyl]-2-(1,1-difluoromethoxy)phenol In analogy to the method described in example B1, 6.9 g (16.4 mmol) of [4-benzyloxy-3-(1.1-difluoromethoxy) benzyl](5-chloro-2,6-dimethylpyrimidin-4-yl)amine (from example A6) are reacted with 70 ml of 12.5N hydrochloric acid in 70 ml of ethanol. Extraction with ethyl acetate at a pH of 8 gives, after concentration, a solid residue. Extraction by stirring with petroleum ether and drying give 2.2 g (41%) of the title compound as a beige crystallizate. m.p.: 167–168.5° C.

In analogy to the method described in example B1, the following compounds are prepared as well:

B8. 2-Bromo-4-[(5-chloro-2,6-dimethylpyrimidin-4-ylamino)methyl]-6-methoxyphenol (m.p.: 191–194° C.)

B9. 4-[(5-Chloro-2,6-dimethylpyrimidin-4-ylamino) methyl]-2-(2,2,2-trifluoroethoxy)phenol (m.p.: 165–168° C.)

B10. (4-Benzyloxy-benzyl)-(5-chloro-pyrimidin-4-yl)-amine 2.1 g (19 mmol) of potassium tert-butylate are added to a suspension of 2.2 g (17.2 mmol) of 5-chloro-pyrimidin-4-ylamine in tert-butanol (50 ml) and the temperature is kept at 60° C. After stirring for 1 h, a solution of 4.1 g (17.2 mmol) of 4-benzyloxy-benzyl chloride in tert-butanol (40 ml) is added dropwise and the reaction mixture is stirred at this temperature for 1 h. The reaction mixture is cooled to room temperature and poured into water (300 ml). The precipitate is filtered off and the filtrate is extracted with ethyl acetate (2×200 ml). The combined organic layers are dried with magnesium sulphate and concentrated in vacuo. The residue is purified by chromatography on silica gel (toluene/dioxane=6:1) to yield 2.0 g (37%) of the title compound as a beige powder of m.p. 95°–100° C.

B11. 2-Allyloxy-4-[(5-chloro-2,6-dimethyl-pyrimidin-4-ylamino)-methyl]-phenol 6.1 g (15 mmol) of (3-allyloxy-4-benzyloxy-benzyl)-(5-chloro-2,6-dimethyl-pyrimidin-4-yl)-amine (from example C7) are added to a solution of conc. HCl (65 ml) and dry ethanol (70 ml) and the reaction is refluxed for 2 h. The mixture is cooled to room temperature, poured into water (700 ml) and neutralized with 6N NaOH. After extraction with ethyl acetate (4×500 ml), the combined organic layers are dried with magnesium sulphate and concentrated in vacuo. The residue is chromatographed on silica gel (toluene/dioxane=20:1) and then recrystallized from ethyl acetate/diisopropyl ether to yield 3.0 g (59%) of the tub compound as a white powder of m.p. 124°–126° C.

C1. 4-[(5-Chloro-2,6-dimethylpyrimidin-4-ylamino) methyl]-2-methylphenol 7.2 ml of a 1M boron tribromide solution (42 mmol) in dichloromethane are added slowly dropwise at room temperature to a solution of 2.05 g (7 mmol) of (5-chloro-2,6-dimethylpyrimidin-4-yl)(4-methoxy-3-methylbenzyl)amino in 45 ml of anhydrous dichloromethane. The mixture is stirred at room temperature for 16 h and then cooled to 4° C. Then, at this temperature, a total of 30 ml of methanol are added slowly dropwise. The solution is subsequently stirred for 10 min and then concentrated. After recrystallization of the solid residue from methanol (65 ml), 1.42 g (73%) of the title compound are isolated as a colorless crystallizate. m.p.: 153° C. (decomposition)

In analogy to the method described in example C1, the following compounds are synthesized:

C2. 4-[(5-Chloro-2,6-dimethylpyrimidin-4-ylamino) methyl]-2-fluorophenol $^1$H NMR (DMSO-d6, δ ppm): 9.8 (sb, OH), 9.45 (t, NH), 7.2–6.8 (m, 3H), 4.65 (d, 1H), 2.52 (s, 3H), 2.45 (s, 3H)

C3. 4-[(5-Chloro-2,6-dimethylpyrimidin-4-ylamino) methyl]-3-fluorophenol (m.p.: 118–120° C.)

C4. 5-[(5-Chloro-2,6-dimethylpyrimidin-4-ylamino) methyl]benzol-1,3-diol (m.p.: 227–230° C.)

C5. 3-[(5-Chloro-2,6-dimethylpyrimidin-4-ylamino) methyl]-5-methoxyphenol

Reaction as for C4 but with only 1 equivalent of boron tribromide. (m.p.: 194–198° C.)

C6. 3-[(5-Chloro-2,6-dimethylpyrimidin-4-ylamino) methyl]-4-fluorophenol (m.p.: 233–234° C. (decomposition))

C7. (3-Allyloxy-4-benzyloxy-benzyl)-(5-chloro-2,6-dimethyl-pyrimidin-4-yl)-amine A mixture of 3.9 g (24 mmol) of 5-chloro-2,8-dimethyl-pyrimidin-4-ylamine, 7.2 g (24 mmol) of 3-allyloxy-4-benzyloxy-benzyl chloride and 3.3 g (26.4 mmol) of potassium tert-butylate in tert-butanol (100 ml) is stirred at 60° C. for 90 min. After cooling to room temperature, the reaction mixture is poured into water (800 ml) and extracted with ethyl acetate (3×400 ml). The combined organic layers are dried with magnesium sulphate and concentrated in vacuo. The residue is chromatographed on silica gel (toluene/dioxane=20:1) and then recrystallized from petroleum ether to yield 9.8 g (78%) of the title compound as a white powder of m.p. 94°–96° C.

Commercial Utility

The excellent activity of compounds of the formula I and their salts against Helicobacter bacteria allows them to be used in human medicine as active principles for treating diseases due to Helicobacter bacteria.

The invention therefore further provides a method of treating mammals, especially humans, who have contracted diseases due to Helicobacter bacteria. The method comprises administering to the individual affected a therapeutically active and pharmacologically tolerated amount of one or more compounds of the formula I end/or their pharmacologically acceptable salts.

The invention further provides the compounds of the formula I and their pharmacologically acceptable salts for use in the treatment of diseases due to Helicobacter bacteria.

The invention likewise embraces the use of compounds of the formula I and their pharmacologically acceptable salts in the preparation of medicaments used for controlling diseases due to Helicobacter bacteria.

The invention additionally provides medicaments for controlling Helicobacter bacteria, comprising one or more compounds of the general formula I and/or their pharmacologically acceptable salts.

Among the Helicobacter strains against which the compounds of the formula I are found effective, mention may be made in particular of the strain Helicobacter pylori, the compounds of the invention being distinguished in particular by high selectivity for Helicobacter microbes.

The medicaments are prepared by conventional methods familiar to the skilled worker. As medicaments, the pharmacologically active compounds of the formula I and their salts (i.e. active principles) are used either as they are or, preferably, in combination with suitable pharmaceutical auxiliaries in the form, for example, of plain tablets, coated tablets, capsules, emulsions, suspensions, gels or solutions, the active principle content being advantageously between 0.1 and 95%.

The choice of suitable auxiliaries for the desired medicament formulations is familiar to the skilled worker on the basis of his or her art knowledge. Besides solvents, gel formers, tableting auxiliaries, and other excipients for the active principle, it is possible, for example, to use antioxidants, dispersants, emulsifiers, defoamers, flavor corrigents, preservatives, solubilizers, colorants or permeation promoters and complexing agents (e.g., cyclodextrins).

The active principles may be administered, for example, parenterally (e.g., intravenously) or, in particular, orally.

In human medicine, in general, the active principles are administered in a daily dose of from about 0.1 to 50, preferably from 1 to 30, mg/kg of body weight, where appropriate in the form of two or more, preferably 2 to 3, individual doses, in particular a single dose daily, in order to achieve the desired result.

The compounds of the invention may also be administered in a fixed or free combination together with a substance which neutralizes gastric acid and/or inhibits gastric acid secretion and/or with a substance suitable for conventional control of Helicobacter pylori.

Examples of gastric acid neutralizers include sodium bicarbonate or other antacids (such as aluminum hydroxide, magnesium aluminate or magaldrate). Examples of gastric acid secretion inhibitors that may be mentioned include $H_2$ blockers (e.g., clmetidine, ranitidine), $H^+/K^+$ ATPase inhibitors (e.g., lansoprazole, omeprazole, esomeprazole, rabeprazole or, in particular, pantoprazole) and what are known as reversible $H^+/K^+$ ATPase inhibitors (compounds as disclosed, for example, in international patent applications WO 00/11000, WO 00/10999, WO 99/55706, WO 99/55705 or WO 98/37080, and structurally similar compounds).

As substances suitable for the conventional control of Helicobacter pylori, mention may be made in particular of antimicrobial substances such as, for example, penicillin G, gentamycin, erythromycin, clarithromycin, azithromycin, nitrofurazone, tinidazole, nitrofurantoin, furazolidon, ampicillin, cefaclor, cefadroxil, cefalexin, cefpodoxime proxetil, cefradine, ceftazidime, ceftriaxone, cefuroxime, ciprofloxacin, clindamycin, doxycycline, ecabet, gatifloxacin, imipenem, meropenem, mezlocillin, minocycline, moxifloxacin, norfloxacin, ofloxacin, oxetacaine, paromomycin, perfloxacin, rebamipide, rifampicin, rifaximin, roxatidine, tetracycline, tiabendazole, trovafloxacin, ritipenem, ecabapide, nitazoxanide, sanfetrinem, sitafloxacin, trospectomycin, metronidazole or amoxycillin, or else bismuth salts such as bismuth citrate, for example.

Biological Investigations

Agar Dilution Test (Determination of the Inhibition of Growth in Vitro on Agar Plates)

The compounds of the formula I were investigated for their activity against Helicobacter pylori in accordance with the methodology described by Tomoyuki Iwahl et al, (Antimicrobial Agents and Chemotherapy, 1991, 490-496) using Columbia agar (Oxoid) over a growth period of 4 days. The compounds investigated gave the approximate $MIC_{60}$, values set out in table A below (the numbers of the compounds indicated correspond to the numbers of examples in the description).

TABLE A

| Compound No. | approx. $MIC_{50}$ (mg/l) |
|---|---|
| 1 | 0.005 |
| 3 | 0.05 |
| 4 | 0.001 |
| 5 | 0.05 |
| 8 | 0.01 |
| 9 | 0.001 |
| 10 | 0.01 |
| 11 | 0.01 |
| 12 | 0.01 |
| 14 | 0.01 |
| 15 | 0.001 |

Determination of the Inhibition of Growth in Vitro in Liquid Culture

The principle of the technique is based on the detection of the multiplication of, for example, Helicobacter pylori in liquid culture using BHI/6% FCS medium. The method ensures linear fluorescence increase in the range from $3\times10^8$ to $3\times10^8$ cells.

The bacterial culture was distributed with an initial density of $1-3\times10^8$ microbes/ml in a 96-well MTP in 100 µl aliquots. The test substances in a concentration of $10^9$ to $10^5$ mol/l in a final concentration of 1% DMSO were added to these minicultures. These MTPs were then incubated under microaerobic conditions (Anaerokult, Merck) and with shaking at 37° C. for 24 hours. Following the 24-hour incubation, the minicultures were transferred to filter MTPs and washed twice with isotonic buffer (filtered off with suction, taken up, shaken) and finally were taken up in double-distilled water and shaken, and an aliquot was transferred to a new MTP. This aliquot was admixed with the fluorescent dye NanoOrange (Molecular Probes) in accordance with the manufacturer's instructions. Development of protein detection took piece at 90° C. in a pressure-secured sandwich technique. After the plates had cooled, the fluorescence was measured on a plate reader at 549 nm. These data were used to construct concentration/effect curves from which the parameters of the substances, the $IC_{50}$ values, were determined. This calculation was made using origin, sigmoidal curve adaptation by means of the 'logistic' algorithm. The compounds investigated in this technique gave the $IC_{50}$ values (the numbers of the compounds indicated correspond to the numbers of examples in the description) set out in table B below.

TABLE B

| Compound No. | $IC_{50}$ (µmol/l) Helicobacter pylori | E. coli |
|---|---|---|
| 1 | 0.026 | >1 |

Determination of the Helicobacter Pylori Eradication Rate in Vivo

Experimental Setup:

Gerbils were infected on days 1, 3, and 5 with a suspension containing 108-109 Helicobacter pylori bacteria per animal. Following infection, the gerbils had a recovery phase of 4 weeks within which the bacteria were able to colonize the stomach. Beginning on day 36, the gerbils were treated on four successive days—three times daily at 07.30, 11.30, and 15.00 hours—with a placebo or the test substance, using a tube. Four weeks after the last treatment, the gerbils were sacrificed using $CO_2$. A tissue sample of the antrum was introduced into the urease test solution and incubated at 37° C. for 24 hours. Changes in color of the solution from yellow to violet, which resulted from the increase in pH caused by the formation of $NH_3$ from the urease, were detected. The eradication rate was calculated as the percentage of animals whose stomach tissue sample gave a negative urease test.

Conditions Under Which the Animals Were Kept:

Groups of 5-10 gerbils per cage (type IV Macrolon cage) were kept at an ambient temperature of 23±2° C. and a relative humidity of 50±10%. They were fed ad libitum with NAFAG feed No. 9439 for rats and mice (NAFAG AG, CH-2900, Gossau, Switzerland) and had free access to mains water during the experiment.

Substances and dosages:

| | |
|---|---|
| Dissolution proportion of the substance: | 4% methylcellulose in water |
| Volume administered: | 10 ml/kg |
| Form of administration: | tube |
| Frequency of administration: | 3 × daily |
| Duration of therapy: | 4 days |

The substances administered are referenced in table C below using numbers which correspond to the numbers of the compounds in the examples.

TABLE C

| Compound No. | Dose administered in mg/kg | Eradication rate in % |
|---|---|---|
| 1 | 50 | 100 |
| 4 | 50 | 100 |
| 8 | 50 | 100 |
| 10 | 50 | 100 |
| 11 | 50 | 100 |
| 16 | 50 | 100 |

What is claimed is:

1. A compound of the formula I,

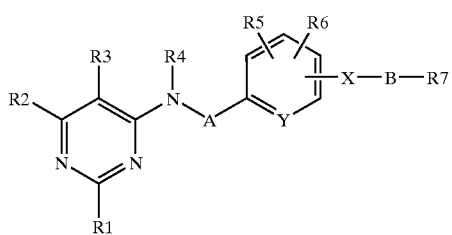

in which
R1 is hydrogen, 1–4C-alkyl or halogen,
R2 is hydrogen, 1–4C-alkyl or halogen,
R3 is hydrogen, 1–4C-alkyl or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, hydroxyl, 1–4C-alkyl, 1–4C-alkoxy, wholly or predominantly fluorine-substituted 1–4C-alkoxy or halogen,
R7 is a cyclic or bicyclic radical which is substituted by nitro and R9 and R10 and is selected from the group consisting of imidazole, imidazopyridazine and imidazopyridine,
A is 1–7C-alkylene,
B is a bond or 1–7C-alkylene,
X is O (oxygen), N-1–4C-alkyl, NH or S(O)$_n$ and
Y is CH or CR8,
where
R8 is hydroxyl, 1–4C-alkyl, 1–4C-alkoxy, wholly or predominantly fluorine-substituted 1–4C-alkoxy, trifluoromethyl or halogen,
R9 is hydrogen, 1–4C-alkyl, halogen, nitro, hydroxy-1–4C-alkyl or 1–4C-alkylcarbonyloxy-1–4C-alkyl,
R10 is hydrogen, 1–4C-alkyl or nitro, and
n is 0, 1 or 2,
or a solvate, hydrate, salt, hydrate of a salt or solvate of a salt thereof.

2. A compound as claimed in claim 1, wherein X is not S(O)$_n$ if at the same time B is a bond and A is methylene and the radicals -A-NR4-(R1)(R2)(R3)-pyrimidin-4-yl and X—B—R7 are in position 3 (meta-position) to one another.

3. A compound as claimed in claim 1, wherein X is O (oxygen).

4. A compound of the formula I as claimed in claim 1, wherein
R1 is hydrogen, 1–4C-alkyl or halogen,
R2 is hydrogen, 1–4C-alkyl or halogen,
R3 is hydrogen or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, 1–4C-alkyl, 1–4C-alkoxy or halogen,
R7 is a cyclic or bicyclic radical which is substituted by nitro and R9 and R10 and is selected from the group consisting of imidazole and imidazopyridazine,
A is methylene,
B is a bond or 1–4C-alkylene,
X is O (oxygen), NH or S(O) and
Y is CH or CR8,
where
R8 is hydroxyl, 1–4C-alkyl, 1–4C-alkoxy, wholly or predominantly fluorine-substituted 1–4C-alkoxy, trifluoromethyl or halogen,
R9 is hydrogen,
R10 is hydrogen,
n is 0,
or a solvate, hydrate, salt, hydrate of a salt or solvate of a salt thereof.

5. A compound as claimed in claim 4, wherein X is not S(O)$_n$ if at the same time B is a bond and the radicals -A-NR4(R1)(R2)(R3)-pyrimidin-4-yl and X—B—R7 are in position 3 (meta-position) to one another.

6. A compound as claimed in claim 4, wherein X is O (oxygen).

7. A compound of the formula I as claimed in claim 1, wherein
R1 is hydrogen or methyl,
R2 is hydrogen or methyl,
R3 is hydrogen or chlorine,
R4 is hydrogen or methyl,
R5 is hydrogen, 1–4C-alkyl, 1–4C-alkoxy, wholly or predominantly fluorine-substituted 1–4C-alkoxy, trifluoromethyl or halogen,
R6 is hydrogen, 1–4C-alkyl, 1–4C-alkoxy or halogen,
R7 is a 3-nitroimidazo[1,2-b]pyridazin-6-yl radical or a 2-methyl-5-nitroimidazol-1-yl radical,
A is methylene,
B is a bond or 1-2C-alkylene,
X is O (oxygen), NH or S, and
Y is CH,
or a solvate, hydrate, salt, hydrate of a salt or solvate of a salt thereof.

8. A compound as claimed in claim 7, wherein X is not S if at the same time B is a bond and the radicals -A-NR4—(R1)(R2)(R3)-pyrimidin-4-yl and X—B—R7 are in position 3 (meta-position) to one another.

9. A compound as claimed in claim 7, wherein X is O (oxygen).

10. A compound of the formula I as claimed in claim 1, wherein B is a bond and R7 is a 3-nitroimidazo[1,2-b]pyridazin-6-yl radical.

11. A compound as claimed in claim 1, characterized by the formula I*

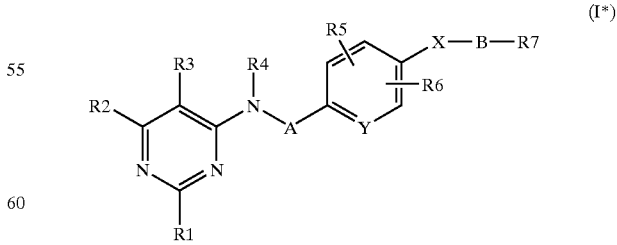

in which
R1 is hydrogen or methyl,
R2 is hydrogen or methyl,
R3 is hydrogen or chlorine, R4 is hydrogen or methyl,
R5 is hydrogen, hydroxyl, methyl, methoxy, ethoxy, cyclopropylmethoxy, isobutoxy, trifluoromethoxy, difluoromethoxy, trifluoromethyl or chlorine,
R6 is hydrogen, methyl, methoxy or chlorine,
R7 is a 3-nitroimidazo[1,2-b]pyridazin-6-yl radical,
A is methylene,
B is a bond,
X is O (oxygen), NH or S, and
Y is CH,
or a solvate, hydrate, salt, hydrate of a salt or solvate of a salt thereof.

12. A compound as claimed in claim 1, characterized by the formula I*

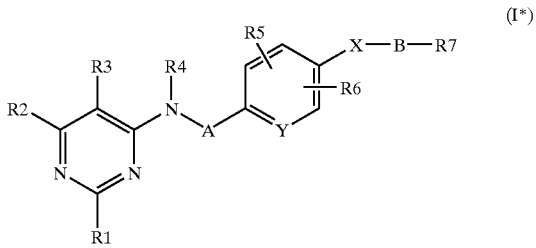

(I*)

in which
R1 is hydrogen or 1–4C-alkyl,
R2 is hydrogen or 1–4C-alkyl,
R3 is hydrogen or chlorine,
R4 is hydrogen,
R5 is hydrogen, hydroxyl, 1–4C-alkyl, 1–4C-alkoxy, wholly or predominantly fluorine-substituted 1–4C-alkoxy or halogen,
R6 is hydrogen or 1–4C-alkoxy,
R7 is a 3-nitroimidazo[1,2-b]pyridazin-6-yl radical,
A is methylene,
B is a bond,
X is O (oxygen) and
Y is CH,
or a solvate, hydrate, salt, hydrate of a salt or solvate of a salt thereof.

13. A compound as claimed in claim 1, characterized by the formula I**

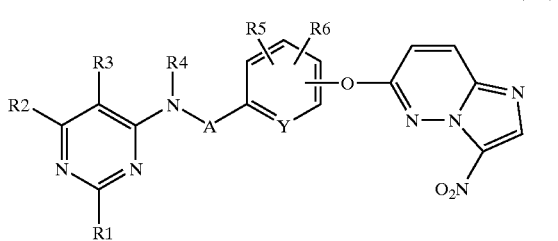

(I**)

in which
R1 is hydrogen, 1–4C-alkyl or halogen,
R2 is hydrogen, 1–4C-alkyl or halogen,
R3 is hydrogen or halogen,
R4 is hydrogen or 1–4C-alkyl,
R5 is hydrogen, hydroxyl, 1–4C-alkyl, 1–4C-alkoxy, wholly or predominantly fluorine-substituted 1–4C-alkoxy, trifluoromethyl or halogen,
R6 is hydrogen, 1–4C-alkyl, 1–4C-alkoxy or halogen,
A is methylene,
Y is CH or CR8,
where
R8 is hydroxyl, 1–4C-alkyl, 1–4C-alkoxy, wholly or predominantly fluorine-substituted 1–4C-alkoxy, trifluoromethyl or halogen,
or a solvate, hydrate, salt, hydrate of a salt or solvate of a salt thereof.

14. A compound as claimed in claim 1, characterized by the formula I**

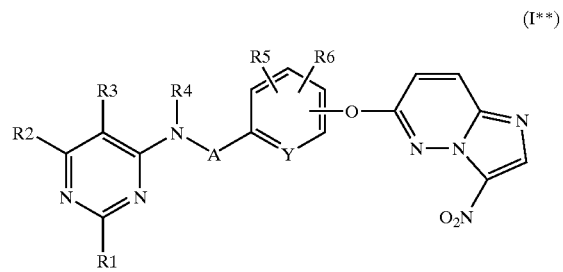

(I**)

in which
R1 is hydrogen or methyl,
R2 is hydrogen or methyl,
R3 is hydrogen or chlorine,
R4 is hydrogen,
R5 is hydrogen, hydroxyl, 1–4C-alkyl, 1–4C-alkoxy, wholly or predominantly fluorine-substituted 1–4C-alkoxy or halogen,
R6 is hydrogen or 1–4C-alkoxy,
A is methylene, and
Y is CH,
or a solvate, hydrate, salt, hydrate of a salt or solvate of a salt thereof.

15. A compound as claimed in claim 1, characterized by the formula I**

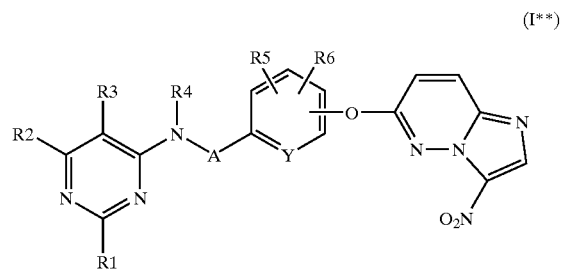

(I**)

in which
R1 is methyl,
R2 is methyl,
R3 is chlorine,
R4 is hydrogen,
R5 is hydrogen, hydroxyl, 1–4C-alkyl, 1–4C-alkoxy, wholly or predominantly fluorine-substituted 1–4C-alkoxy or halogen,
R6 is hydrogen or 1–4C-alkoxy,
A is methylene, and
Y is CH,
or a solvate, hydrate, salt, hydrate of a salt or solvate of a salt thereof.

16. A compound as claimed in claim 1, characterized by the formula I**

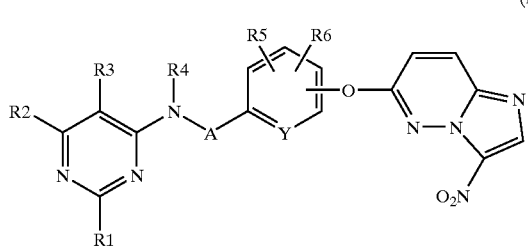

(I**)

in which
R1 is methyl,
R2 is methyl,
R3 is chlorine,
R4 is hydrogen,
R5 is hydrogen, hydroxyl, methyl, methoxy, cyclopropylmethoxy, 2,2,2-trifluoroethoxy, difluoromethoxy, fluorine, chlorine or bromine,
R6 is hydrogen or methoxy,
A is methylene, and
Y is CH,
or a solvate, hydrate, salt, hydrate of a salt or solvate of a salt thereof.

17. A compound of claim 1, which is (5-chloro-2,6-dimethylpyrimidin-4-yl)[4-(3-nitroimidazo[1,2-b]pyridazin-6-yloxy)-benzyl]amine, or a solvate, hydrate, salt, hydrate of a salt or solvate of a salt thereof.

18. A compound of formula I as claimed in claim 2, wherein B is a bond and R7 is a 3-nitroimidazo[1,2-b]pyridazin-6-yl radical.

19. A compound of formula I as claimed in claim 3, wherein B is a bond and R7 is a 3-nitroimidazo[1,2-b]pyridazin-6-yl radical.

20. A compound of formula I as claimed in claim 4, wherein B is a bond and R7 is a 3-nitroimidazo[1,2-b]pyridazin-6-yl radical.

21. A compound of formula I as claimed in claim 5, wherein B is a bond and R7 is a 3-nitroimidazo[1,2-b]pyridazin-6-yl radical.

22. A compound of formula I as claimed in claim 6, wherein B is a bond and R7 is a 3-nitroimidazo[1,2-b]pyridazin-6-yl radical.

23. A compound of formula I as claimed in claim 7, wherein B is a bond and R7 is a 3-nitroimidazo[1,2-b]pyridazin-6-yl radical.

24. A compound of formula I as claimed in claim 8, wherein B is a bond and R7 is a 3-nitroimidazo[1,2-b]pyridazin-6-yl radical.

25. A compound of formula I as claimed in claim 9, wherein B is a bond and R7 is a 3-nitroimidazo[1,2-b]pyridazin-6-yl radical.

26. A pharmaceutical composition comprising one or more compounds of formula I as claimed in claim 1 and/or a pharmaceutically acceptable solvate, hydrate, salt, hydrate of a salt or solvate of a salt thereof, together with a suitable pharmaceutical auxiliary.

27. A method of treating a disease or disorder due to Helicobacter bacteria in a patient comprising administering to a patient in need thereof a therapeutically effective amount of one or more compounds of formula I as claimed in claim 1 and/or a pharmaceutically acceptable solvate, hydrate, salt, hydrate of a salt or solvate of a salt thereof.

* * * * *

UNITED STATES PATENT AND TRADEMARK OFFICE
CERTIFICATE OF CORRECTION

PATENT NO. : 6,818,642 B2
DATED : November 16, 2004
INVENTOR(S) : Grundler

It is certified that error appears in the above-identified patent and that said Letters Patent is hereby corrected as shown below:

Column 22,
Line 2, please delete "S(O)" and replace with -- $S(O)_n$ --
Line 16, please delete "-A-NR4(R1)(R2)(R3)-pyrimidin-4-yl" and replace with -- -A-NR4-(R1)(R2)(R3)-pyrimidin-4-yl --

Signed and Sealed this

Fifteenth Day of February, 2005

JON W. DUDAS
*Director of the United States Patent and Trademark Office*